United States Patent
Zobel et al.

(10) Patent No.: US 6,395,546 B1
(45) Date of Patent: May 28, 2002

(54) GENERATION OF DOPAMINERGIC NEURONS FROM HUMAN NERVOUS SYSTEM STEM CELLS

(75) Inventors: Rita Zobel, Tartu (EE); Michel F. Levesque, Beverly Hills, CA (US)

(73) Assignee: NeuroGeneration, Inc., Los Angeles, CA (US)

( * ) Notice: Subject to any disclaimer, the term of this patent is extended or adjusted under 35 U.S.C. 154(b) by 0 days.

(21) Appl. No.: 09/490,569

(22) Filed: Feb. 1, 2000

(51) Int. Cl.⁷ ................................................. C12N 5/08
(52) U.S. Cl. ........................................ 435/377; 435/368
(58) Field of Search ................................ 435/368, 377, 435/455; 536/24.5

(56) References Cited

U.S. PATENT DOCUMENTS

| | | | | |
|---|---|---|---|---|
| 5,411,883 A | * | 5/1995 | Boss et al. | 435/240.2 |
| 5,753,491 A | | 5/1998 | Major et al. | 435/240.2 |
| 5,981,165 A | * | 11/1999 | Weiss et al. | 435/4 |
| 6,040,180 A | * | 3/2000 | Johe | 435/377 |

FOREIGN PATENT DOCUMENTS

| | | |
|---|---|---|
| WO | WO 00/61729 | 10/2000 |

OTHER PUBLICATIONS

Wagner, J. et al., "Induction of a midbrain dopaminergic phenotype in Nurr 1–overexpressing neural stem cells by type 1 astrocytes," *Nature Biotechnology*, vol. 17, pp. 653–659 (1999).

K. Brubaker et al., "All–trans retinoic acid affects the expression of orphan receptors COUP–TFI and COUP–TFII in the developing neural tube," *Developmental Brain Research*, vol. 93, pp. 198–202 (1996).

R. M. E. Chalmers–Redman et al., "In Vitro Proagation and Inducible differentiation of Mulitpotential Progenitor Cells From Human Fetal Brain," *Neuoscience*, vol. 76, No. 4, pp. 1121–1128 (1997).

C. Lois et al., "Proliferating subventricular zone cells in the adult mammalian forebrain can differentiate into neurons and glia," *Proc. Natl. Acad. Sci. USA.*, vol. 90, pp. 2074–2077 (Mar. 1993).

C. Lois et al., "Long–Distance Neuronal Migration in the Adult Mammalian Brain," *Science*, vol. 264, pp. 1145–1148 (May 20, 1994).

C. M. Morshead et al., "Postmitotic Death is the Fate of Constitutively Proliferating Cells in the Suependymal Layer of the Adult Mouse Brain," *The Journal of Neuroscience*, vol. 12, No. 1, pp. 249–256 (Jan. 1992).

C. M. Morshead et al., "Neural Stem Cells in the Adult Mammalian Forebrain: A Relatively Quiescent Subpopulation of Subependymal Cells," *Neuron*, vol. 13, pp. 1071–1082 (Nov. 1994).

K. Neuman et al., "Orphan Receptor Coup–TFI Antagonizes Retinoic Acid–Induced Neuronal Differentiation," *Journal of Neuroscience Research*, vol. 41, pp. 39–48 (1995).

B. A. Reynolds et al., "Generation of Neurons and Astocytes from Isolated Cells of the Adult Mammalian Central Nervous System," *Science*, vol. 255, pp. 1707–1710 (Mar. 27, 1992).

A. Soosaar et al., "Cell type specific regulation of COUP–TF II promoter activity," *FEBS Letters*, vol. 391, pp. 95–100 (1996).

C. N. Svendsen et al., "Survival and Differentiation of Rat and Human Elpidermal Growth Factor–Responsive Precursor Cells Following Grafting into the Lesioned Adult Central Nervous System," *Experimental Neurology*, vol. 137, Article No. 0039, pp. 376–388 (1996).

S. Weiss et al., "Multipotent CNS Stem Cells are Present in the Adult Mammalian Spinal Cord and Ventricular Neuroaxis," *The Journal of Neuroscience*, vol. 16, No. 23, pp. 7599–7609 (Dec. 1, 1996).

S. Weiss et al., "Is there a neural stem cell in the mammalian forebrain?," *TINS*, vol. 19, No. 9, pp. 387–393 (1996).

\* cited by examiner

*Primary Examiner*—Remy Yucel
*Assistant Examiner*—Bronwen M. Loeb
(74) *Attorney, Agent, or Firm*—Knobbe, Martens, Olson & Bear, LLP

(57) ABSTRACT

The present invention relates to methods for generating dopaminergic neurons in vitro from embryonic and adult central nervous system cells. Specifically, these cells are isolated, cultured in vitro and stimulated to differentiate into dopaminergic neurons by down-regulating COUP-TFI and/or COUP-TFII expression or increasing NOT1 expression. These newly generated dopaminergic neurons may serve as an excellent source for cell replacement therapy in neurological disorders in which the dopaminergic system is compromised.

9 Claims, No Drawings

GENERATION OF DOPAMINERGIC NEURONS FROM HUMAN NERVOUS SYSTEM STEM CELLS

FIELD OF THE INVENTION

The present invention relates to methods for generating dopaminergic neurons in vitro from embryonic and adult central nervous system cells. Specifically, these cells are isolated, cultured in vitro and stimulated to differentiate into dopaminergic neurons by down-regulating COUP-TFI and/or COUP-TFII expression or increasing NOT1 expression. These newly generated dopaminergic neurons may serve as an excellent source for cell replacement therapy in neurological disorders in which the dopaminergic system is compromised.

BACKGROUND OF THE INVENTION

The mammalian central nervous system is a highly diversified neural network of cells that form intricate intercellular connections. Once these neural cells are damaged, they do not typically regenerate. Accordingly, treatment of neurological disorders, such as neurodegenerative diseases and neurotrauma, has focused on replacing damaged neural cells with healthy cells. A major obstacle in the field of neuronal transplantation is the inadequacy of donor material. In recent years, therapeutic transplantations have been performed using human fetal tissue as the donor substrate. In addition to the controversial ethical dilemmas that surround the use of human fetal tissue, there are also critical methodological difficulties. Because fetal tissue is obtained from freshly aborted fetuses, there is a limited supply of available tissue. Further, the recipient may immunologically reject the fetal tissue, once transplanted. Moreover, transplanting fresh fetal tissue may result in the transmission of infectious diseases. Even with extensive screening of fetal tissue, certain infections, such as HIV, may not yet be present at clinically significant levels and may go undetected during the screening process. Because of the significant obstacles inherent to fetal tissue transplantation, alternative sources of neuronal cells, especially cells that can be used for autologous transplantation, would be a breakthrough in the field of neuroscience. A renewable source of normal human neural cells would be an indispensable tool in clinical studies of neurotrauma and neurodegenerative diseases. Further, the use of such cells may eliminate the need for fetal human tissue in therapeutic approaches aimed at restoring neurological function by transplantation of nervous system cells.

Central nervous system stem cells represent a renewable source of human neural cells, which may eliminate the need for fetal human tissue in restoring neurological function by intracerbral and intraspinal transplantation. Nervous system stem cells have been isolated from human embryonic and adult brain (Svendsen et al., 1996; Chalmers-Redman et al., 1997). Multipotent stem cells are present in the entire ventricular neuraxis of the adult mammalian central nervous system, including the spinal cord (Morshead and van der Kooy, 1992; Reyolds and Weiss, 1992; Lois and Alvarez-buylla, 1993, 1994; Morshead et al., 1994; Weiss et al., 1996a, b). In response to certain growth factors such as epidermal growth factor (EGF), basic fibroblast growth factor (bFGF) and leukemia inhibitory factor (LIF), these stem cells can be made to proliferate and differentiate into neuronal cells (neurons) and glial cells (astrocytes and oligodendrocytes) (Reynolds and Weiss, 1992; Morshead et al., 1994; Weiss et al., 1996b).

Although propagation and subsequent transplantation of stem cells derived from adult brain tissue represents an advancement in the field of neurology, methods to differentiate these progenitor cells into specific neuronal populations are required in order to use these cells as a stable source of transplant material. The present invention describes a novel method to induce stem cells to express catecholaminergic neuronal features and, specifically, to produce dopamine. These newly generated dopaminergic neurons may serve as an excellent source for cell replacement therapy in neurological disorders, such as Parkinson's disease, in which the dopaminergic system is compromised.

SUMMARY OF THE INVENTION

In the preferred embodiment of this invention, dopaminergic neurons are generated in vitro by initially isolating human neuronal stem cells from fetal or adult central nervous system tissue. These stem cells are then cultured in the presence of growth factors such as bFGF and leukemia inhibitory factor LIF. The growth factors are subsequently removed and the cells are treated with chemicals that stimulate initial differentiation, such as all-trans retinoic acid and dibutyryl cAMP. The expression of chicken ovalbumin upstream promoter transcription factor (COUP-TF) is then inhibited to induce specific differentiation of dopaminergic neurons. Specifically down-regulating COUP-TFI and/or COUP-TFII expression by using antisense oligonucleotides directed to COUP-TF sequences stimulates differentiation into dopaminergic neurons. It is believed that this differentiation into dopaminergic neurons is due to the increased activity of NOT1 when it is released from inhibition by COUP-TF factors. Thus in another embodiment of the invention neuronal stem cells are stimulated to differentiate into dopaminergic neurons by stimulating NOT1 activity in vitro.

DETAILED DESCRIPTION OF THE PREFERRED EMBODIMENTS

Cell transplant therapy is of particular relevance to neurodegenerative disorders. We recently demonstrated that stem cells isolated by our methods survive transplantation into the adult rodent brain and differentiate into neurons and glia with no subsequent tumor formation. The present invention provides a method for generating specific types of neuronal cells and, as such, will be particularly useful in treating neurological disorders that involve degeneration of specific populations of neurons. For example, Parkinson's disease is a neurological illness characterized by the progressive destruction of dopaminergic neurons. Current efforts in treating Parkinson's have focused on the transplantation of dopaminergic neurons obtained from aborted fetuses. The present invention provides for a reliable source of transplant material and avoids the numerous ethical and technical difficulties inherent in fetal tissue transplantation.

The cells generated by the method of the present invention will also be useful in drug discovery. The effect of potential therapeutics on dopaminergic neurons will be able to be tested in vitro. In addition, the present invention allows for individualized testing of drugs. A culture of a patients own neurons can be tested and the most beneficial therapeutics chosen.

The present invention addresses the need in the previous technology by providing a system for generating dopaminergic neurons in vitro from embryonic and adult mammalian central nervous system cells. Specifically, this invention reveals that down regulating the expression of COUP-TFI and/or COUP-TFII in neuronal stem cells in vitro can induce the development of dopaminergic neurons.

During differentiation of human neuronal stem cells, expression of COUP-TF is induced. Depending on the stem cell isolate, COUP-TFI, COUP-TFII, or both are expressed at a high level. COUP-TF factors function as negative transcriptional regulators of NOT1/RXR and thus when COUP-TF factors are present, the heterodimer complex NOT1/RXR is inactive. Accordingly, down-regulating COUP-TF expression stimulates NOT1 activity. NOT1 function appears to be essential for the development of dopaminergic neurons. Thus stimulation of NOT1 via the suppression of COUP-TF factors may induce the development of dopaminergic neurons. The present invention reveals that down-regulating COUP-TFI and/or COUP-TFII expression in neuronal stem cells in vitro results in the development of a large number of dopaminergic neurons. While we believe that the stimulation of NOT1 contributes to the differentiation of neuronal stem cells into dopaminergic neurons, it is likely that other mechanisms contribute to or are wholly responsible for this process. Thus the present invention is not limited to differentiation of dopaminergic neurons from neuronal stem cells through the stimulation of NOT1.

Differentiation of Dopaminergic Neurons

Neuronal development requires the orchestrated action of numerous molecular processes including epigenetic signaling and activation of specific transcription factor systems. During development, neuronal stem cells develop into specific neuronal cell types depending on the signals they receive from the surrounding cells. Development of dopaminergic neurons depends on the sequential activity of extracellular signaling molecules, including BMP4(2,6), FGF4/FGF8, sonic hedgehog aminoterminal peptide and glial derived neurotrophic factor. These signaling molecules activate a cascade of transcription factors, which in turn activate the specific genes that are responsible for the development of the dopaminergic phenotype.

Certain transcription factors are critical to the development of dopaminergic neurons. These include MASH1/NeuroD, Phox2a,b, Ptx3 and NOT1. NOT1 is a member of the nuclear hormone receptor superfamily of transcription factors that are essential regulators of numerous developmental processes. NOT1 forms heterodimers with RXR transcription factors to regulate transcription of target genes including enzymes necessary for dopamine synthesis. Studies have revealed that the inactivation of the mouse homologue of NOT1 (Nurr1) results in the loss of dopaminergic neurons in the substantia nigra, suggesting that the activity of NOT1 is essential for development of dopaminergic neurons. Another family of nuclear hormone receptors is the COUP-TF orphan receptors. COUP-TF factors function as negative regulators of NOT1/RXR heterodimers. As we have demonstrated, down-regulation of COUP-TF factor expression affects the development of dopaminergic neurons, possibly through the subsequent release of NOT1 from inhibition.

Differentiation of Human Central Nervous System Stem Cells Induces Expression of Orphan Nuclear Hormone Receptors COUP-TFI and COUP-TFII When induced to differentiate with all-trans retinoic acid or a similar stimulating agent, human central nervous system stem cells develop into a variety of neuronal cell types, including dopaminergic neurons. The ratio of developing dopaminergic neurons, however, remains relatively low in these culture conditions; approximately 4–5% of all neurons and 1–2% of all cells in these cultures are dopaminergic neurons.

Studies have demonstrated that retinoic acid induces expression of COUP-TFI and COUP-TFII (Soosaar et al., 1995) and that COUP-TF transcription factors can block neuronal differentiation (Neuman et al., 1995). Analyses of Northern blots as described in Example 1 demonstrate that COUP-TF expression is highly induced in human central nervous system stem cells after initiation of differentiation by all-trans retinoic acid. Depending on the stem cell culture, COUP-TFI, COUP-TFII or both may be highly induced. Induction of expression of COUP-TF factors during the early phases of stem cell differentiation indicates that differentiation pathways that depend on nuclear hormone receptors (i.e. dopaminergic neurons require NOT1) may be regulated via regulation of these transcription factors.

EXAMPLE 1

For Northern blots, 25 $\mu$g of total RNA was fractionated on 1.2% agarose-formaldehyde gel and transferred to a nylon membrane (Hybond N, Amersham). New cDNAs were radiolabeled ($^{32}$P) using the Multiprime DNA labeling system (Amersham) and used as probes. The blots were washed at high stringency (0.2×SSC, 65° C.) and exposed to X-ray film. The amount and quality of transferred RNA were monitored by methylene blue staining of the filters before hybridization. Quantification of Northern blot data was done by using phosphorimager technology (Molecular Dynamics). Statistical analyses (standard deviations and T-tests) were performed to evaluate the significance of observed changes in mRNA levels and were applied to the RNase protection and Northern blot data.

COUP-TF Factors Interfere with the Transcriptional Activation by NOT1

NOT1 functions as a transcriptional activator and induces promoter activity of several genes that contain binding sites for NOT1 or NOT1/RXR heterodimers. This invention reveals that COUP-TF factors act as transcriptional repressors and suppress activity of NOT1. We performed transient co-transfection assays using different combinations of COUP-TF factors, NOT1 and RXR. The bacterial chloramphenicol acetyl transferase (CAT) gene was used as a reporter by linking it to promoter constructs that contained binding sites for NOT1 and NOT1/RXR heterodimers. This assay is described in Example 2. Results of these experiments demonstrate that COUP-TF factors suppress transcriptional activity of both NOT1 and NOT1/RXR heterodimers.

EXAMPLE 2

Cells were transfected with plasmid DNA containing different promoter constructs using the LipofectaAMINE (Gibco) transfection protocol. The LipofectaAMINE transfection protocol was used to transfect about 1–5% of the neurons in hippocampal and cortical cultures. Cells were harvested 24 or 48 hours later and processed for CAT assay. CAT assay data were quantified using phosphorimager technology.

Antisense Oligonucleotides Down-Regulate Expression of COUP-TF Factors

As described in more detail below, the present invention reveals that down-regulating COUP-TF expression during the initial phases of human stem cell differentiation in vitro stimulates differentiation of dopaminergic neurons. We first demonstrated that antisense oligonucleotides can down-regulate COUP-TF factor expression. A series of antisense oligonucleotides was generated corresponding to different sequences of COUP-TFI and COUP-TFII, as described in Example 3. We tested the effectiveness of these oligonucleotides on reducing the expression of COUP-TF factor protein. Expression was measured using Western blot analysis. The present invention demonstrates that two oligonucleotides, TF1 and TF2, corresponding to the region of translational initiation, down-regulate COUP-TF expression very efficiently; other tested antisense oligonucleotides are less efficient. However, it will be recognized by one skilled in the art that other antisense oligonucleotides may be effective at down-regulating COUP-TF expression. Randomly synthesized oligonucleotides were used as controls in all experiments.

EXAMPLE 3

Antisense oligonucleotides were directly added to the culture media at the concentration of 5–10 µM. Randomly synthesized oligonucleotides and oligonucleotides corresponding to the sequence of human albumin were used as controls. Thio-modified oligonucleotides were synthesized and used in these studies to increase the stability of the oligonucleotides in the culture media and cells.

The human COUP-TFI antisense oligonucleotide sequence was:
  5'-TGCGGATCTCGCCAGCTGCTAACTACCATTG CCAT (SEQ ID NO: 1) (Genbank accession number NM—005654)

The human COUP-TFII antisense oligonucleotide sequence was:
  5'-CTGGGGTCGCGCCACGTGCTGCCAT (SEQ ID NO: 2) Genbank accession number U60477)

Down-Regulating Expression of COUP-TF Factors Potentiates Transcriptional Activation of NOT1 in Transient Assays The present invention reveals that the antisense oligonucleotides TF1 and TF2, described in Example 3, can release NOT1 from the inhibitory effects of COUP-TF factors. Co-transfection of COUP-TF expression constructs with NOT1 and RXR expression constructs into teratocarcinoma and human stem cells suppresses the activity of test promoters with NOT1 and NOT1/RXR binding sites in CAT assays, as described in Example 2. Treating cells with antisense oligonucleotides against COUP-TF restores the activity of NOT1 and NOT1/RXR complexes. Thus down-regulation of COUP-TF factors stimulates NOT1 activity.

Culture of Central Nervous System Stem Cells

The effect of down-regulating COUP-TF factor expression and the subsequent stimulation of NOT1 was examined in neuronal stem cells in vitro. Cells used in this invention must be properly isolated and cultured before initiating differentiation. The preferred methods of stem cell isolation and culture are set forth in Example 4. However, one of ordinary skill in the art will appreciate that any other method of obtaining or isolating stem cells is also within the scope of the present invention. In the near future it may be possible to purchase neuronal stem cells from a commercial source. If the dopaminergic neurons resulting from the practice of the invention are to be used in transplantation, it is preferable to start with neuronal stem cells obtained from the patient. This reduces the chance that the cells will be immunologically rejected and that a disease such as HIV will be transmitted to the patient through the transplanted cells.

EXAMPLE 4

Fetal or surgically removed adult human brain tissue was placed into ice-cold DMEM/F-12 containing penicillin streptomycin for further dissection. The tissue was cut into small pieces (~1 mm$^3$) and transferred into trypsin solution (0.02 mg/ml) in Verseen (GIBCO) and incubated at 37° C. for 15 minutes. After incubation, a trypsin inhibitor mixture (Clonetics) was added and the tissue triturated mechanically with a Pasteur pipette. The cell suspension was centrifuged at 400 rpm for 5 minutes and the pellet washed once with DMEM/F-12. The cells were then plated at a density of 5,000–10,000 viable cells/ml in 6 well Nunc tissue culture dishes in media composed of DMEM/F-12 (1:1) containing Hepes buffer, glucose, sodium bicarbonate and glutamine. The media was supplemented with B27 supplement (Gibco), bFGF (20 ng/ml) (PeproTech, Inc.) and LIF (20 ng/ml) (PeproTech, Inc.).

Human CNS stem cells were grown in F12/DMEM serum free media (GIBCO) supplemented with B27 growth supplement (GIBCO), 20 ng/ml of human recombinant bFGF and LIF (both from PeproTech, Inc.). CNS stem cells were grown as neurospheres in 25 cm$^2$ or 75 cm$^2$ Falcon tissue culture flasks. The media was changed every second day and the neurospheres were dissociated by mechanical trituration every 12–15 days.

The neurospheres can be cultured for many months in the presence of the growth factors. For clinical applications, such as autologous transplantation, the cells must be cultured for at least 4–6 months to obtain sufficient numbers of cells for the procedure.

Down-Regulating Expression of COUP-TF Factors in Differentiating Human Central Nervous System Stem Cells Stimulates Differentiation of Dopaminergic Neurons COUP-TF factors can suppress the transcriptional activity of NOT1 and, in turn, stimulate the differentiation of neuronal stem cells into dopaminergic neurons. The preferred method of stimulating differentiation of stem cells into dopaminergic neurons is described in Example 5. The present invention reveals that down-regulating both COUP-TFI and/or COUP-TFII during the initial phases of differentiation (preferably during the first 3 days) results in significant increases in the number of differentiating dopaminergic neurons which express tyrosine hydroxylase and dopamine-beta decarboxylase as described below. We also demonstrated using RT-PCR and RNase protection analyses that expression of dopamine transporter is significantly elevated. RNase protection assays were performed using an RNase protection assay kit (Ambicon). In control cultures, only 1–2% of total cells differentiate into dopaminergic neurons. In the present invention, 25–30% of total cells (60–70% of neurons) in cultures treated with COUP-TF antisense oligonucleotides develop into dopaminergic neurons. The present invention is not limited to the down-regulation of COUP-TF factors through the use of antisense oligonucleotides. One skilled in the art will recognize that there are other suitable ways of down-regulating COUP-TF factors to promote differentiation of neuronal stem cells into dopaminergic neurons in vitro. These other methods include but are not limited to the use of antisense expression constructs.

EXAMPLE 5

Neuronal stem cells are dissociated into smaller aggregates of 50–200 cells by mechanical trituration in growth media. Approximately 2×10⁶ cells are plated on 100 mm tissue culture plates. To begin differentiation, the media is replaced with F12/DMEM serum free media (GIBCO) supplemented with B27 growth supplement (GIBCO), $10^{-6}$ M all-trans retinoic acid, 1 mM dibutyryl cyclic AMP, and 5 μM COUP-TF antisense oligonucleotides. Differentiation was analyzed after 7 days.

Analyses of Differentiation

Dopaminergic differentiation of stem cells after down-regulation of COUP-TF factors was evaluated using immunohistochemical detection of several marker proteins that are characteristic for dopaminergic neurons. Tyrosine hydroxylase and dopamine-beta-decarboxylase were monitored in the method described in Example 6. The synthesis of dopamine and the release of dopamine by the dopaminergic cells in response to a depolarization was monitored in the method described in Example 7. One of ordinary skill in the art will understand that analysis of other dopaminergic markers are also within the scope of the present invention.

EXAMPLE 6

Cells were fixed with 4% paraformaldehyde and processed according to the immunohistochemical detection protocol recommended by the antibody manufacturer. Immunoreactive cells were counted using fluorescent microscope. Dopaminergic differentiation of stem cells was monitored using immunohistochemical detection of tyrosine hydroxylase and dopamine-beta-decarboxylase. Additionally RT-PCR and RNase protection analyses were used to identify dopaminergic transporter expression.

EXAMPLE 7

The synthesis and secretion of dopamine in differentiated cultures was analyzed. Reverse-phase HPLC analyses demonstrated that differentiated cells synthesize and secrete dopamine. Dopamine concentration in the culture media of differentiated cells 5 days after initiation of differentiation was 100±45 pg/ml. Stimulation of dopamine secretion by exposing cultures to 50 mM KCl for 30 minutes led to an approximately 3 fold increase in dopamine levels in the culture media (345±74 pg/ml).

For the BPLC analysis 1 ml of growth media was collected. Dopamine was stabilized by the immediate addition of 88 μl of 85% orthophosphoric acid and 4.4 mg of metabisulfite. Samples were analyzed by standard HPLC procedures. Dopamine was extracted from samples using the aluminum extraction method and analyzed with a reverse-phase C18 column in a MD-TM mobile phase (Esa, Inc.). Results were validated by co-elution with dopamine standards.

Stimulating NOT1 Activity Promotes the Differentiation of Neuronal Stem Cells into Dopaminergic Neurons In Vitro Differentiation of neuronal stem cells into dopaminergic neurons in vitro appears to result from the stimulation of NOT1. Thus another aspect of the present invention is the generation of dopaminergic neurons in vitro through the stimulation of NOT1 activity in neuronal stem cells. One skilled in the art will recognize that there are many different ways to stimulate NOT1 activity. The present invention is not limited to any specific method of stimulating NOT1 activity.

What is claimed is:

1. A method of generating dopaminergic neuronal cells comprising:

obtaining stem cells from mammalian central nervous system tissue;

culturing said stem cells in vitro; and down-regulating COUP-TFI and/or COUP-TFII expression in said stem cells, thereby generating said dopaminergic neuronal cells.

2. The method of claim 1 wherein said stem cells are cultured in the presence of one or more growth factors, said one or more growth factors being selected from the group consisting of epidermal growth factor (EGF), basic fibroblast growth factor (bFGF), and leukemia inhibitory factor (LIF).

3. The method of claim 1 wherein said stem cells are induced to begin differentiating into neuronal cell types by the addition of one or more chemicals to said cultures, said chemicals being selected from the group consisting of all-trans retinoic acid and dibutyryl cAMP.

4. The method of claim 1 wherein said stem cells are obtained from fetal or juvenile central nervous system tissue.

5. The method of claim 1 wherein said stem cells are obtained from adult central nervous system tissue.

6. The method of claim 1 in which COUP-TFI and/or COUP-TFII expression is down-regulated using antisense oligonucleotides directed to COUP-TFI and/or COUP-TFII.

7. The method of claim 1 wherein said stem cells are obtained by:

dissecting central nervous system tissue;

incubating said tissue with trypsin solution;

adding trypsin inhibitor;

mechanically triturating said tissue; and centrifuging said tissue.

8. The method of claim 1 wherein said stem cells are obtained from human tissue.

9. The method of claim 2 wherein said stem cells are caused to begin differentiating into neuronal cell types by withdrawing said one or more growth factors.

* * * * *

```
                        SEQUENCE LISTING

<160> NUMBER OF SEQ ID NOS: 2

<210> SEQ ID NO 1
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 1
tgcggatctc gccagctgct aactaccatt gccat                          35

<210> SEQ ID NO 2
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 2
ctggggtcgc gccacgtgct gccat                                     25
```